(12) United States Patent
Lamberth et al.

(10) Patent No.: US 7,166,746 B2
(45) Date of Patent: Jan. 23, 2007

(54) N-BISARYL- AND N-ARYL-CYCLOAKYLIDENYL-αHYDROXY- AND α-ALKOXY ACID AMIDES

(75) Inventors: Clemens Lamberth, Basel (CH); Martin Zeller, Muenchwilen (CH); Tibor Goegh, Bratislava (SK)

(73) Assignee: Syngenta Crop Protection, Inc., Greensboro, NC (US)

( * ) Notice: Subject to any disclaimer, the term of this patent is extended or adjusted under 35 U.S.C. 154(b) by 163 days.

(21) Appl. No.: 10/522,077

(22) PCT Filed: Jul. 23, 2003

(86) PCT No.: PCT/EP03/08057

§ 371 (c)(1),
(2), (4) Date: Jan. 21, 2005

(87) PCT Pub. No.: WO2004/011417

PCT Pub. Date: Feb. 1, 2004

(65) Prior Publication Data

US 2005/0245607 A1 Nov. 3, 2005

(30) Foreign Application Priority Data

Jul. 24, 2002 (GB) .................................. 0217211.2

(51) Int. Cl.
C07C 233/58 (2006.01)
A01N 37/18 (2006.01)

(52) U.S. Cl. ...................... 564/184; 564/170; 564/185; 564/186; 558/410; 549/77; 549/496; 546/334; 546/335; 546/336; 546/337; 514/357; 514/438; 514/461; 514/617

(58) Field of Classification Search ................ 514/357, 514/410, 438, 461, 520, 617; 546/334, 335, 546/336, 337; 549/77, 496; 558/410; 564/170, 564/184, 185, 186
See application file for complete search history.

(56) References Cited

U.S. PATENT DOCUMENTS 3,803,232 A 4/1974 Blatter et al.
6,469,005 B1 * 10/2002 Zeller et al. ................ 514/248

FOREIGN PATENT DOCUMENTS

| EP | 0940387 | 9/1999 |
| WO | WO 9429267 | 12/1994 |
| WO | WO 9617840 | 6/1996 |
| WO | WO 0041998 | 7/2000 |
| WO | WO 03078382 | 9/2003 |

OTHER PUBLICATIONS

Chiellini et al, Biorganic & Medicinal chemistry, vol. 10, 333-346, 2002.*

Nachtsheim C M et al: Asymmetrische Reduktive Aminierung Von Cycloalkanonen, Cis-1S, 2S-2-Arylcyclohexanamin Asymmetric Reducti.vol. 322, No. 4, Apr. 1 1989; pp. 187-197.

Database Crossfire Beilstein Institut Zur Forderung Der Chemischen Wissenschaften, Reaction ID 470534; Abstarct & Smith et al: J. Org Chem., 23, 1958, pp. 524-526.

Database Crossfire Beilstein Online! Beilstein institut Zur Forderung Der Chemischen Wissenchaften, Reaction ID 273427, Abstract & Copp; Walls; J. Chem. Soc., 1950, p. 311, 315, 316.

Database Crossfire Beilstein 'Online! Beilstein Institut Zur Forderung Der Chemischen Wissenchaftrn, Frankfurt; Reaction ID 2206083; Abstarct & Matsumoto, Masakatsu et al. vol. 24, No. 10, 1994; pp. 1441-1446.

Database Crossfire Belstein "Online" Beilstein Institut Zur Forderung Der Chemischen Wissenchaften, Frankfurt; Reaction ID 21267; Abstract & Bell; Kenyon; J. Chem. Soc., 1926; p. 2712.

Database Crossfire Beilstein Online! Beilstein Institut Zur Forderung Der Chemischen Wissenchaften, Frankfurt; Reaction ID 7285501; Abstract & Mikhant'Ev: Radziunas; Tr. Probl. Lab. Khim. Vysokomol.; 1964, p. 14.

Database Crossfire Beilstein 'Online! Beilstein Institut Zur Forderung Der Chemischen Wissenchaften, Frankfurt; Reaction ID 30776; Abstract & Trefilowa; Postowskii; Dokl. Akad. Nauk SSSR., 114, 1957, p. 116.

Database Crossfire Beilstein Online! Beilstein Institut Zur Forderung Der Chemischen Wissenchaften, Frankfurt; Accession No. BRN 3097900; Abstract & Acoria; Scarlata; Ann. Chim (Rome), 58, 1968, p. 32.

(Continued)

*Primary Examiner*—Shailendra Kumar
(74) *Attorney, Agent, or Firm*—William A. Teoli, Jr.

(57) ABSTRACT

The invention relates to N-bisaryl- and N-aryl-cycloalkylidenyl-a-hydroxy- and a-alkoxy acetic acid amides of the general formula (I) including the optical isomers thereof and mixtures of such isomers, wherein $R_1$ is hydrogen, $C_1$–$C_{12}$alkyl; $C_2$–$C_{12}$alkenyl; $C_2$–$C_{12}$alkynyl; $C_1$–$C_{12}$haloalkyl; $R_2$ is hydrogen; optionally substituted alkyl; or optionally substituted alkynyl; $R_3$ is optionally substituted aryl or optionally substituted heteroaryl; A is an optionally substituted saturated or unsaturated $C_3$–$C_8$-cycloalkylidene, optionally substituted phenylidene or optionally substituted saturated or unsaturated heterocyclylidene bridge, $R_4$ and $R_5$ are each independently hydrogen or an organic radical, and $R_6$ is hydrogen; tri-$C_1$–$C_4$alkyl-silyl; di-$C_1$–$C_4$alkyl-phenylsilyl; $C_1$–$C_4$alkyl-diphenylsilyl; triphenylsilyl; optionally substituted alkyl; optionally substituted alkenyl or optionally substituted alkynyl. The compounds possess plant-protecting properties and are suitable for protecting plants against infestation by phytopathogenic microorganism, especially fungi.

(I)

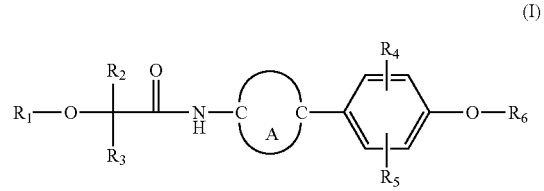

13 Claims, No Drawings

OTHER PUBLICATIONS

Database Crossfire Beilstein 'Online! Beilstein Institu Zur Forderung Der Chemischen Wissenchaften, Frankfurt; Accession No. BRN 7589821; Abstract & Tetrahedron Lett., vol. 38, No. 3: 1997, pp. 399-402.

Database CA 'Online! Chemical Abstracts Service, Columbus, Ohio, US; DE GEE, A. et al: Stereospectific Synthesis of Chiral N-(P-Methoxyphenylalkyl)Pyridinium; Retrieved From STN: Accession No. 81:3733, Abstract & J. Chem. Soc. Perkin Trans 1: Organic and Bio-Organic Chemistry (1972-1999): No. 6. 1974, pp. 676-679.

Database CA 'Online! Chemical Abstracts Service, Columbus, Ohio, US; Trager, W. F.; Huitric, A.C.: "CIS-and Trans-2-(3,4,5-Trimethoxyphenyl)Cyclohexylamine"; Database Accession No. 63:88571: J. Pharmaceutical Science, vol. 54, No. 10, 1965, pp. 1552-1553.

\* cited by examiner

N-BISARYL- AND N-ARYL-CYCLOAKYLIDENYL-αHYDROXY- AND α-ALKOXY ACID AMIDES

This application is a 371 of International Application No. PCT/EP03/08057 filed Jul. 23, 2003, which claims priority to GB 0217211.2 filed Jul. 24, 2002, the contents of which are incorporated herein by reference.

The present invention relates to novel N-aryl-cycloalkylidenyl-α-hydroxy- and α-alkoxy acetic acid amides of formula I below. It relates to the preparation of these substances and to agrochemical compositions comprising at least one of those compounds as active ingredient. The invention relates also to the preparation of the said compositions and to the use of the compounds or of the compositions in controlling or preventing the infestation of plants by phytopathogenic microorganisms, especially fungi.

The invention relates to N-aryl-cycloalkylidenyl-α-hydroxy- and α-alkoxy acetic acid amides of the general formula I

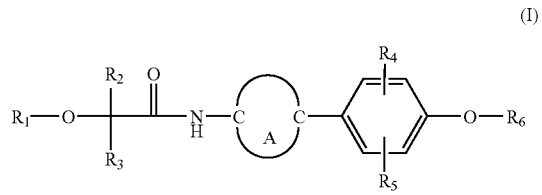

including the optical isomers thereof and mixtures of such isomers, wherein $R_1$ is hydrogen, $C_1$–$C_{12}$alkenyl; $C_2$–$C_{12}$alkynyl; $C_1$–$C_{12}$haloalkyl;

$R_2$ is hydrogen; $C_1$–$C_4$alkyl; $C_1$–$C_4$haloalkyl; $C_2$–$C_5$alkenyl or $C_2$–$C_5$alkynyl;

$R_3$ is aryl or heteroaryl, each optionally substituted with substituents selected from the group comprising $C_1$-$C_8$alkyl, $C_2$-$C_8$alkenyl, $C_2$-$C_8$alkynyl, $C_3$–$C_8$cycloalkyl, $C_3$-$C_8$cycloalkyl-$C_1$-$C_4$alkyl, phenyl and phenyl$C_1$-$C_4$alkyl, where all these groups may be substituted with one or more halogen atoms; $C_1$-$C_8$alkoxy, $C_3$-$C_8$alkenyloxy; $C_3$-$C_8$alkynyloxy; $C_1$-$C_8$alkoxy-$C_1$-$C_4$alkyl; $C_1$-$C_8$haloalkyl, $C_1$-$C_8$alkylthio; $C_1$-$C_8$haloalkylthio, $C_1$-$C_8$alkylsulfonyl; formyl; $C_1$-$C_8$alkanoyl; hydroxy; cyano; nitro; amino; $C_1$-$C_8$alkylamino; $C_1$-$C_8$dialkylamino; carboxyl; $C_1$-$C_8$alkoxycarbonyl; $C_3$-$C_8$alkenyloxycarbonyl and $C_3$-$C_8$alkynyloxycarbonyl; or A is a 1,2-cyclohexylidene or 1,2-cyclopropylidene bridge, $R_4$ is hydrogen $C_1$–$C_8$alkyl; $C_2$–$C_8$alkenyl; $C_2$–$C_8$alkynyl; $C_3$–$C_8$cycloalkyl; $C_3$–$C_8$cycloalkyl-$C_1$–$C_4$alkyl; $C_1$–$C_8$alkylthio; $C_1$–$C_8$alkylsulfonyl; $C_1$–$C_8$alkoxy; $C_3$–$C_8$alkenyloxy; $C_3$–$C_8$alkylnyloxy; $C_3$–$C_8$cycloalkoxy; $C_1$–$C_8$alkoxy-$C_1$–$C_4$alkyl; $C_1$–$C_8$alkoxycarbonyl; $C_3$–$C_8$alkenyloxycarbonyl; $C_3$–$C_8$alkynyloxycarbonyl; $C_1$–$C_8$alkanoyl; $C_1$–$C_8$dialkylamino or $C_1$–$C_8$alkylamino, wherein turn the alkyl, alkenyl, alkynyl or cycloalkyl moieties may be partially or fully halogenated; or is carboxyl; formyl; halogen; nitro; cyano; hydroxy or amino; and $R_5$ is hydrogen; $C_1$–$C_8$alkyl; $C_2$–$C_8$alkenyl; $C_2$–$C_8$alkynyl; $C_3$–$C_8$cycloalkyl; $C_3$–$C_8$cycloalkyl-$C_1$–$C_4$alkyl; $C_1$–$C_8$alkylthio; $C_1$–$C_8$alkylsulfonyl; $C_1$–$C_8$alkoxy; $C_3$-$C_8$alkenyloxy; $C_3$–$C_8$alkylnyloxy; $C_3$–$C_8$cycloalkoxy; $C_1$–$C_8$alkoxy-$C_1$–$C_4$alkyl; $C_1$–$C_8$alkoxycarbonyl; $C_3$–$C_8$alkenyloxycarbonyl; $C_3$–$C_8$alkynyloxycarbonyl; $C_1$–$C_8$alkanoyl; $C_1$–$C_8$dialkylamino or $C_1$–$C_8$alkylamino, wherein in turn the alkyl, alkenyl, alkynyl or cycloalkyl moieties may be partially or fully halogenated; or is carboxyl; formyl; halogen; nitro; cyano; hydroxy or amino; and $R_6$ is propargyl.

In the above definitions "halogen" includes fluorine, chlorine, bromine and iodine. Likewise, the prefix "halo" Includes fluorine, chlorine, bromine and iodine.

The alkyl, alkenyl and alkynyl radicals may be straight-chain or branched. This applies also to the alkyl, alkenyl or alkynyl parts of other alkyl-, alkenyl- or alkynyl-containing groups.

Depending upon the number of carbon atoms mentioned, alkyl on its own or as part of another substituent is to be understood as being, for example, methyl, ethyl, propyl, butyl, pentyl, hex, heptyl, octyl, nonyl, decyl, undecyl, dodecyl and the isomers thereof, for example isopropyl, isobutyl, tert-butyl or sec-butyl, isopentyl or tert-pentyl.

Depending upon the number of carbon atoms mentioned, alkenyl as a group or as a structural element of other groups is to be understood as being, for example, ethenyl, allyl, 1-propenyl, buten-2-yl, buten-3-yl, penten-1-yl, penten-3-yl, hexen-1-yl, 4-methyl-3-pentenyl or 4-methyl-3-hexenyl.

Alkynyl as a group or as a structural element of other groups is, for example, ethynyl, propyn-1-yl, propyn-2-yl, butyn-1-yl, butyn-2-yl, 1-methyl-2-butynyl, hexyn-1-yl, 1-ethyl-2-butynyl or octyn-1-yl.

Optionally substituted alkyl, alkenyl or alkynyl groups may carry one or more substituents selected from halogen, alkyl, alkoxy, alkylthio, cycloalkyl, phenyl, nitro, cyano, hydroxy, mercapto, alkylcarbonyl and alkoxycarbonyl. Preferably, the number of substituents is not more than three with the exception of halogen, where e.g. the alkyl groups may be perhalogenated.

Heteroaryl stands for aromatic ring systems comprising mono-, bi- or tricyclic systems being formed by 1 or 2 five- to six-membered condensed rings wherein at least one oxygen, nitrogen or sulfur atom is present as a ring member. Typically heteroaryl comprises 1 to 4 identical or different heteroatoms selected from nitrogen, oxygen and sulfur, wherein the number of oxygen and sulfur atoms normally does not exceed one. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

The above heteroaryl groups may carry one or more identical or different substituents. Normally not more than three substituents are present at the same time. Examples of substituents of aryl or heteroaryl groups are: alkyl, alkenyl, alkynyl, cycloalkyl, cycloalkylalkyl, phenyl and phenylalkyl, it being possible in turn for all of the preceding-groups to carry one or more identical or different halogen atoms; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl or alkynyloxycarbonyl.

The organic radical in $R_4$ and $R_5$ indicates that practically every substituent used in the art of organic chemistry may be placed in the indicated position at the phenylene bridge member. Preferred are however the more frequently used radicals like $C_1$–$C_8$alkyl; $C_2$–$C_8$alkenyl; $C_2$–$C_8$alkynyl; $C_3$–$C_8$cycloalkyl; $C_3$–$C_8$cycloalkyl-$C_1$–$C_4$alkyl; $C_1$–$C_8$alkylthio; $C_1$–$C_8$alkylsulfonyl; $C_1$–$C_8$alkoxy; $C_3$–$C_8$alkenyloxy; $C_3$–$C_8$alkynyloxy; $C_3$–$C_8$cycloalkoxy; $C_1$–$C_8$alkoxy-$C_1$–$C_4$alkyl; $C_1$–$C_8$alkoxycarbonyl; $C_3$–$C_8$alkenyloxycarbonyl; $C_1$–$C_8$alkynyloxycarbonyl; $C_1$–$C_8$alkanoyl; $C_1$–$C_8$dialkylamino or $C_1$–$C_8$alkylamino, wherein in each of the above radicals the alkyl, alkenyl, alkynyl or cycloalkyl moieties may be partially or fully halogenated; or like carboxyl; formyl; halogen; nitro; cyano; hydroxy or amino.

Cycloalkyl is, depending upon the number of carbon atoms mentioned, cyclopropyl, cyclobutyl, cyclopentyl, cyclohexyl, cycloheptyl or cyclooctyl.

A haloalkyl group may contain one or more (identical or different) halogen atoms, and for example may stand for $CHCl_2$, $CH_2F$, $CCl_3$, $CH_2Cl$, $CHF_2$, $CF_3$, $CH_2CH_2Br$, $C_2Cl_5$, $C_2F_5$, $CH_2Br$, $CHClBr$, $CF_3CH_2$, etc.

The presence of at least one asymmetric carbon atom and/or at least one asymmetric oxidized sulfur atom in the compounds of formula I means that the compounds may occur in optically isomeric forms. As a result of the presence of a possible aliphatic C=C double bond, geometric isomerism may also occur. Formula I is intended to include all those possible isomeric forms and mixtures thereof.

Preferred subgroups of compounds of formula I are those wherein $R_1$ is hydrogen; $C_1$–$C_{12}$alkyl, $C_2$–$C_{12}$alkenyl; or $C_2$–$C_{12}$alkynyl; or $R_1$ is hydrogen; $C_1$–$C_4$alkyl or $C_2$–$C_5$alkynyl; or $R_1$ is hydrogen or $C_2$–$C_5$alkynyl; or $R_1$ is hydrogen or propargyl; or $R_1$ is propargyl; or $R_2$ is hydrogen or $C_1$–$C_4$alkyl; or $R_2$ is hydrogen; or $R_3$ is phenyl, naphthyl, biphenyl, thienyl or pyridyl, each optionally substituted by one to three substituents selected from the group comprising $C_1$–$C_8$alkyl; $C_2$–$C_8$alkenyl; $C_2$–$C_8$alkynyl; $C_1$–$C_8$haloalkyl; $C_1$–$C_8$alkoxy; $C_1$–$C_8$haloalkoxy; $C_1$–$C_8$alkylthio; $C_1$–$C_8$haloalkylthio; $C_1$–$C_8$alkylsulfonyl; halogen; cyano; nitro and $C_1$–$C_8$alkoxycarbonyl; or $R_3$ is phenyl, naphthyl, thienyl or pyridyl, each optionally substituted by one to three substituents selected from the group comprising $C_1$–$C_6$alkyl; $C_1$–$C_6$haloalkyl; $C_1$–$C_6$alkoxy; $C_1$–$C_6$haloalkoxy; $C_1$–$C_6$alkylthio; $C_1$–$C_6$haloalkylthio; halogen and $C_1$–$C_6$alkoxycarbonyl; or $R_3$ is thienyl or pyridyl, each optionally substituted by one to two substituents selected from the group comprising methyl, fluoro, chloro or bromo; or $R_3$ is phenyl optionally substituted by one to two substituents selected from the group comprising methyl, ethyl, methoxy, fluoro, chloro, bromo, phenyl, trifluoromethyl, trifluoromethylthio or trifluoromethoxy; or $R_3$ is phenyl optionally substituted by one to two substituents selected from the group comprising fluoro, chloro and bromo, or is phenyl optionally substituted by one substituent selected from the group comprising methyl, ethyl, methoxy, phenyl, trifluoromethyl, trifluoromethylthio or trifluoromethoxy; or A is or 1,2-cyclohexylidene; or $R_4$ is hydrogen; $C_1$–$C_8$alkyl; $C_1$–$C_8$haloalkyl; $C_2$–$C_8$alkenyl; $C_2$–$C_8$alkynyl; $C_1$–$C_8$alkylthio; $C_1$–$C_8$haloalkylthio; $C_1$–$C_8$alkoxy; $C_1$–$C_8$haloalkoxy; $C_1$–$C_8$alkoxy-$C_1$–$C_4$alkyl; $C_1$–$C_8$alkoxycarbonyl; $C_1$–$C_8$alkanoyl; formyl; halogen; nitro; cyano or hydroxy; or $R_4$ is hydrogen; $C_1$–$C_4$alkyl; $C_1$–$C_4$alkoxy; $C_1$–$C_4$haloalkoxy or halogen; or $R_4$ is hydrogen; methoxy or ethoxy; or $R_5$ is hydrogen; $C_1$–$C_4$alkyl; $C_1$–$C_4$haloalkyl; $C_1$–$C_4$alkoxy; $C_1$–$C_4$alkoxycarbonyl; $C_1$–$C_4$alkanoyl; formyl; halogen; cyano or hydroxy; or $R_5$ is hydrogen; $C_1$–$C_4$alkyl; halogen or cyano; or $R_5$ is hydrogen.

Further preferred subgroups of the compounds of formula I are those wherein

1) $R_1$ is hydrogen; $C_1$–$C_{12}$alkyl; $C_2$–$C_{12}$alkenyl; $C_2$–$C_{12}$alkynyl or $C_1$–$C_{12}$haloalkyl; and $R_2$ is hydrogen and $R_3$ is phenyl; naphthyl or heteroaryl formed by 1 or 2 five- or six-membered rings containing 1 to 4 identical or different heteroatoms selected from oxygen, nitrogen or sulfur, wherein each aromatic rings is optionally mono- or poly-substituted with $C_1$–$C_8$alkyl, $C_2$–$C_8$alkenyl, $C_2$–$C_8$alkynyl, $C_3$–$C_8$cycloalkyl, $C_1$–$C_8$alkoxy, $C_3$–$C_8$alkenyloxy, $C_3$–$C_8$alkynyloxy, $C_3$–$C_8$cycloalkyloxy, $C_1$–$C_8$alkylthio, $C_1$–$C_8$alkylsulfonyl, $C_1$–$C_8$alkanoyl, $C_1$–$C_8$alkylamino, $C_3$–$C_8$alkenyloxycarbonyl, $C_3$–$C_8$alkynyloxycarbonyl, $C_1$–$C_8$dialkylamino, $C_1$–$C_8$alkylamino, wherein in turn the alkyl, alkenyl, alkynyl or cycloalkyl moieties may be partially or fully halogenated, or with halogen, nitro, cyano, hydroxy or amino; and A is a 1,2-cyclohexylidene or 1,2-cyclopropylidene bridge, and $R_4$ is hydrogen; $C_1$–$C_8$alkyl; $C_2$–$C_8$alkenyl; $C_2$–$C_8$alkynyl; $C_3$–$C_8$cycloalkyl; $C_3$–$C_8$cycloalkyl-$C_1$–$C_4$alkyl; $C_1$–$C_8$alkylthio; $C_1$–$C_8$alkylsulfonyl; $C_1$–$C_8$alkoxy; $C_3$–$C_8$alkenyloxy; $C_3$–$C_8$alkynyloxy; $C_3$–$C_8$cycloalkoxy; $C_1$–$C_8$alkoxy-$C_1$–$C_4$alkyl; $C_1$–$C_8$alkoxycarbonyl; $C_3$–$C_8$alkenyloxycarbonyl; $C_3$–$C_8$alkynyloxycarbonyl; $C_1$–$C_8$alkanoyl; $C_1$–$C_8$dialkylamino or $C_1$–$C_8$alkylamino, wherein in turn the alkyl, alkenyl, alkynyl or cycloalkyl moieties may be partially or fully halogenated; or is carboxyl; formyl; halogen; nitro; cyano; hydroxy or amino; and $R_5$ is hydrogen; $C_1$–$C_8$alkyl; $C_2$–$C_8$alkenyl; $C_2$–$C_8$alkynyl; $C_3$–$C_8$cycloalkyl; $C_3$–$C_8$cycloalkyl-$C_1$–$C_4$alkyl; $C_1$–$C_8$alkylthio; $C_1$–$C_8$alkylsulfonyl; $C_1$–$C_8$alkoxy; $C_3$–$C_8$cycloalkoxy; $C_3$–$C_8$alkynyloxy; $C_3$–$C_8$cycloalkoxy; $C_1$–$C_8$alkoxy-$C_1$–$C_4$alkyl; $C_1$–$C_8$alkoxycarbonyl; $C_3$–$C_8$alkenyloxycarbonyl; $C_3$–$C_8$alkynyloxycarbonyl; $C_1$–$C_8$alkanoyl; $C_1$–$C_8$dialkylamino or $C_1$–$C_8$alkylamino, wherein in turn the alkyl, alkenyl, alkynyl or cycloalkyl moieties may be partially or fully halogenated; or is carboxyl; formyl; halogen; nitro; cyano; hydroxy or amino; and $R_6$ is propargyl; or 2) $R_1$ is hydrogen, $C_1$–$C_{12}$alkyl, $C_2$–$C_{12}$alkynyl or $C_1$–$C_{12}$haloalkyl; and $R_2$ is hydrogen and $R_3$ is phenyl, naphthyl, furyl, thienyl, imidazolyl, thiazolyl, oxazolyl, pyridyl, pyrimidinyl, benzothienyl, benzothiazolyl chinolinyl, pyrazolyl, indolyl, benzimidazolyl or pyrrolyl, wherein each of the aromatic rings is optionally substituted with 1 to 3 substituents selected from $C_1$–$C_8$alkyl, $C_2$–$C_8$alkenyl, $C_3$–$C_8$cycloalkyl, $C_1$–$C_8$alkoxy, $C_1$–$C_8$alkylthio, $C_1$–$C_8$alkoxycarbonyl, $C_1$–$C_8$haloalkyl, $C_1$–$C_8$haloalkoxy, $C_1$–$C_8$haloalkylthio, halogen, nitro or cyano; and A is A is a 1,2-cyclohexylidene or 1,2-cyclopropylidene bridge, and $R_4$ is hydrogen; $C_1$–$C_8$alkyl; $C_1$–$C_8$haloalkyl; $C_2$–$C_8$alkenyl; $C_2$–$C_8$alkynyl; $C_1$–$C_8$alkylthio; $C_1$–$C_8$haloalkylthio; $C_1$–$C_8$alkoxy; $C_1$–$C_8$haloalkoxy; $C_1$–$C_8$alkoxy- $C_1$–$C_4$alkyl; $C_1$–$C_8$alkoxycarbonyl; $C_1$–$C_8$alkanoyl; formyl; halogen; nitro; cyano or hydroxy; and $R_5$ is hydrogen; $C_1$–$C_4$alkyl; $C_1$–$C_4$haloalkyl; $C_1$–$C_4$alkoxy; $C_1$–$C_4$alkoxycarbonyl; $C_1$–$C_4$alkanoyl; formyl; halogen; cyano or hydroxy; and $R_6$ is propargyl; or 3) $R_1$ is hydrogen, $C_1$–$C_4$alkyl, or $C_2$–$C_5$alkynyl; and $R_2$ is hydrogen and $R_3$ is phenyl or phenyl substituted with 1 to 3 substituents selected from $C_1$–$C_8$alkyl, $C_2$–$C_8$alkenyl, $C_3$–$C_8$cycloalkyl, $C_1$–$C_8$alkoxy, $C_1$–$C_8$alkylthio, $C_1$–$C_8$alkoxycarbonyl, $C_1$–$C_8$haloalkyl, $C_1$–$C_8$haloalkoxy, $C_1$–$C_8$haloalkylthio, halogen, nitro or cyano; and A is A is a 1,2-cyclohexylidene or 1,2-cyclopropylidene bridge, and $R_4$ is hydrogen; $C_1$–$C_4$alkyl; $C_1$–$C_4$alkoxy; $C_1$–$C_4$haloalkoxy or halogen; and $R_5$ is hydrogen; $C_1$–$C_4$alkyl; halogen or cyano; and $R_6$ is propargyl ; or 5) $R_1$ is hydrogen or $C_2$–$C_5$alkynyl; and $R_2$ is hydrogen and $R_3$ is phenyl; $C_{1-4}$alkylphenyl or halophenyl; and A is 1,2-cyclohexylidene or 1,2-cyclopropylidene; and $R_4$ is hydrogen; methoxy or ethoxy; and $R_5$ is hydrogen; and $R_6$ is propargyl ; or 6) $R_1$ is hydrogen or propargyl; and $R_2$ is hydrogen; and $R_3$ is phenyl optionally substituted by one to two substituents selected from the group comprising methyl, ethyl, methoxy, fluoro, chloro, bromo, phenyl, trifluoromethyl, trifluoromethylthio or trifluoromethoxy; and A is 1,2-cyclohexylidene; and $R_4$ is hydrogen or methoxy; and $R_5$ is hydrogen; and $R_6$ is propargyl; or 7) $R_1$ is propargyl; and $R_2$ is hydrogen; and $R_3$ is phenyl optionally substituted by one to two substituents selected from the group comprising fluoro, chloro and bromo, or is phenyl optionally substituted by one substituent selected from the group comprising methyl, ethyl, methoxy, phenyl, trifluoromethyl, trifluoromethylthio or trifluoromethoxy; and A is 1,2-cyclohexylidene; and $R_4$ is hydrogen or methoxy; and $R_5$ is hydrogen; and $R_6$ is propargyl.

Preferred individual compounds are:

2-hydroxy-N-[trans-2-(3-methoxy-4-prop-2-ynyloxy-phenyl)-cyclohexyl]-2-phenyl-acetamide, 2-(4-chlorophenyl)-9-hydroxy-N-[trans-2-(3-methoxy-4-prop-2-ynyloxy-phenyl)-cyclohexyl]-acetamide, 2-(4-bromophenyl)-2-hydroxy-N-[trans-2-(3-methoxy-4-prop-2-ynyloxy-phenyl)-cyclohexyl]-acetamide, 2-(3,4-dichlorophenyl)-2-hydroxy-N-[trans-2-(3-methoxy-4-prop-2-ynyloxy-phenyl)-cyclohexyl]-acetamide, N-[trans-2-(3-methoxy-4-prop-2-ynyloxy-phenyl)-cyclohexyl-2-phenyl-2-prop-2-ynyloxy-acetamide, 2-(4-chlorophenyl)-N-[trans-2-(3-methoxy-4-prop-2-ynyloxy-phenyl)-cyclohexyl]-2-prop-2-ynyloxy-acetamide, 2-(4-bromophenyl)-N-[trans-2-(3-methoxy-4-prop-2-ynyloxy-phenyl)-cyclohexyl]-2-prop-2-ynyloxy-acetamide, and 2-(3,4dichlorophenyl)-N-[trans-2-(3-methoxy-4-prop-2-ynyloxy-phenyl)-cyclohexyl]-2-prop-2ynyloxy-acetamide. -ynyloxy-acetamide.

Certain α-hydroxy- and α-alkoxy acid derivatives with a distinct chemical structure have been proposed for controlling plant-destructive fungi (for example in WO 94/29267 and WO 96/17840). The action of those preparations is not, however, satisfactory in all aspects of agricultural needs. Surprisingly, with the compound structure of formula I, new kinds of microbiocides having a high level of activity have been found.

The N-aryl-heterocyclylidenyl- and N-aryl-cycloalkylidenyl-α-hydroxy- and α-alkoxy acid amides of formula I may be obtained according to one of the following processes:

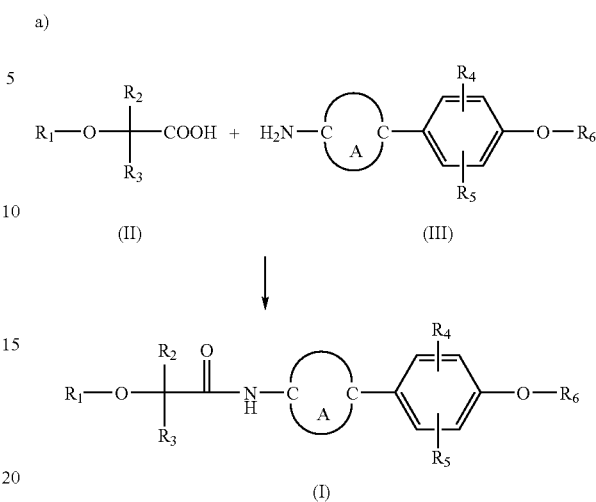

a)

An α-hydroxy- or α-alkoxy acid of formula II or a carboxyl-activated derivative of an α-hydroxy- or α-alkoxy acid of formula II wherein $R_1$, $R_2$ and $R_3$ are as defined for formula I, is reacted with an amine of formula III wherein A, $R_4$, $R_5$ and $R_6$, are as defined for formula I, optionally in the presence of a base and optionally in the presence of a diluting agent. Carboxyl-activated derivatives of the α-hydroxy- or α-alkoxy acid of formula II encompasses all compounds having an activated carboxyl group like an acid halide, such as an acid chloride or an acid fluoride, like symmetrical or mixed anhydrides, such as mixed anhydrides with O-alkylcarbonates, like activated esters, such as p-nitrophenylesters or N-hydroxysuccinimidesters, as well as in situ produced activated forms of the amino acid of formula. It by condensating agents, such as dicyclohexylcarbodiimide, carbonylduimidazol, benzotriazol-1-yloxy-tris(dimethylamino)phosphonium hexafluorophosphate, O-benzotriazol-1-yl N,N,N', N'-bis(pentamethylene)uronium hexafluorophosphate, O-benzotriazol-1-yl N,N,N',N'-bis-(tetramethylene)uronium hexafluorophosphate, O-benzotriazol-1-yl N,N,N',N'-tetramethyluronium hexafluorophosphate or benzotriazol-1-yloxy-tripyrrolidinophosphonium hexafluorophosphate. The mixed anhydrides of the α-hydroxy- or α-alkoxy acids of the formula II can be prepared by reaction of a α-hydroxy- or α-alkoxy acid of formula II with chloroformic acid esters like chloroformic acid alkylesters, such as ethyl chloroformate or isobutyl chloroformate, optionally in the presence of an organic or inorganic base like a tertiary amine, such as triethylamine, N,N-diisopropyl-ethylamine, pyridine, N-methyl-piperidine or N-methyl-morpholine. The acid halide of the α-hydroxy- or α-alkoxy acids -of formula II may be prepared by reaction of a α-hydroxy- or α-alkoxy acid of formula II with an inorganic halide, such as thionyl chloride or phosphorous pentachloride, or with organic halides, such as phosgene or oxalyl chloride.

The present reaction is preferably performed in an inert solvent like aromatic, non-aromatic or halogenated hydrocarbons, such as chlorohydrocarbons e.g. dichloromethane or toluene; ketones e.g. acetone; esters e.g. ethyl acetate; amides e.g. N,N-dimethylformamide; nitriles e.g. acetonitrile; or ethers e.g. diethylether, tert-butyl-methylether, dioxane or tetrahydrofuran or water. It is also possible to use mixtures of these solvents. The reaction is performed optionally in the presence of an organic or inorganic base like a tertiary amine, e.g. triethylamine, N,N-diisopropyl-ethylamine, pyridine, N-methyl-piperidine or N-methylmorpholine, like a metal hydroxide or a metal carbonate, preferentially an alkali hydroxide or an alkali carbonate, such as lithium hydroxide, sodium hydroxide or potassium hydroxide at temperatures ranging from −80 to +150° C., preferentially at temperatures ranging from −40 to +40° C.

b)

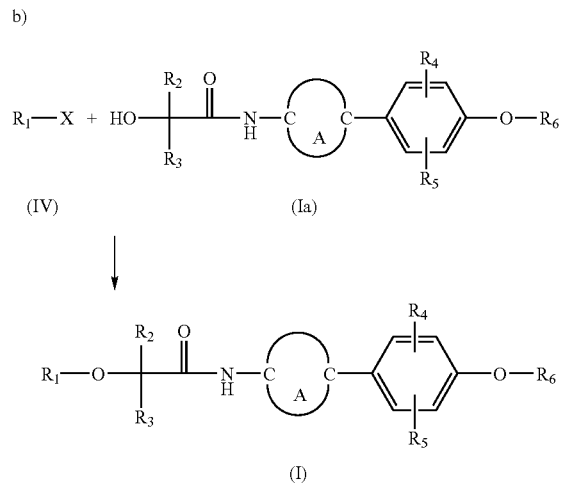

Compounds of formula I, in which $R_1$ is different from hydrogen; may also be prepared by reaction of a α-hydroxy acid amide of formula Ia wherein A, $R_2$, $R_3$, $R_4$, $R_5$ and $R_6$ are as defined for formula I, with a compound of formula IV wherein $R_1$ is as defined for formula I with the exception of hydrogen and where X is a leaving group like a halide such as a chloride or bromide, or a sulfonic ester such as a tosylate, mesylate or triflate.

The reaction is preferably performed in an inert solvent like aromatic, non-aromatic or halogenated hydrocarbons, such as chlorohydrocarbons e.g. dichloromethane or toluene; ketones e.g. acetone; esters e.g. ethyl acetate; amides e.g. N,N-dimethylformamide; nitriles e.g. acetonitrile; or ethers e.g. diethylether, tert-butyl-methylether, dioxane or tetrahydrofuran or water. It is also possible to use mixtures of these solvents. The reaction is performed optionally in the presence of an organic or inorganic base like a tertiary amine, e.g. triethylamine, N,N-diisopropyl-ethylamine, pyridine, N-methyl-piperidine or N-methyl-morpholine, like a metal hydroxide or a metal carbonate, preferentially an alkali hydroxide or an alkali carbonate, such as lithium hydroxide, sodium hydroxide or potassium hydroxide at temperatures ranging from −80 to +150° C., preferentially at temperatures ranging from 40 to +40° C.

c)

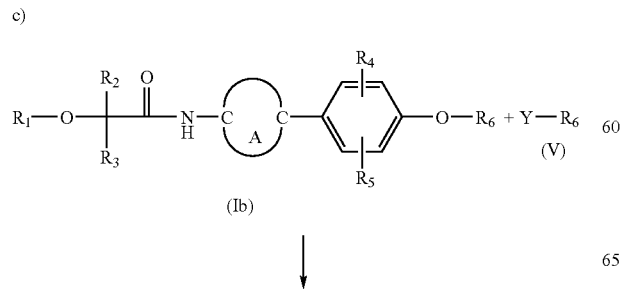

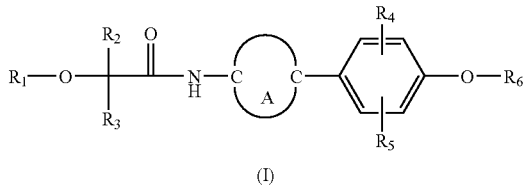

The compounds of formula I, where $R_1$ is different from hydrogen, may also be prepared by reaction of a phenol of formula Ib where A, $R_1$, $R_2$, $R_3$, $R_4$, and $R_5$ are as defined for formula I, with a compound of formula V where $R_8$ is as defined for formula I with the exception of hydrogen and where Y is a leaving group like a halide such as a chloride or bromide or a sulfonic ester such as a tosylate, mesylate or triflate.

The reaction is performed in an inert solvent like aromatic, non-aromatic or halogenated hydrocarbons, such as chlorohydrocarbons e.g. dichloromethane or toluene; ketones e.g. acetone or 2-butanone; esters e.g. ethyl acetate; ethers e.g. diethylether, tert-butyl-methylether, dioxane or tetrahydrofuran, amides e.g. dimethylformamide, nitriles e.g. acetonitrile, alcohols e.g. methanol; ethanol, isopropanol; n-butanol or tert-butanol, sulfoxides e.g. dimethylsulfoxide or water. It is also possible to use mixtures of these solvents. The reaction is performed optionally in the presence of an organic or inorganic base like a tertiary amine, such as triethylamine, N,N-diisopropyl-ethylamine, pyridine, N-methyl-piperidine or N-methyl-morpholine, like a metal hydroxide, a metal carbonate or a metal alkoxide, preferentially an alkali hydroxide, an alkali carbonate or an alkali alkoxide, such as lithium hydroxide, sodium hydroxide, potassium hydroxide, sodium carbonate, potassium carbonate, sodium methoxide, potassium methoxide, sodium ethoxide, potassium ethoxide, sodium tert-butoxide or potassium tert-butoxide at temperatures ranging from −80 to +20° C., preferentially at temperatures ranging from 0 to +120° C.

Preparation of compounds of formula III, illustrated with one example of the phenylidene series where A is phenylidene yielding the aromatic amines of formula IIIa, but also simulating a model for an aryl or an aromatic heterocyclic bridge:

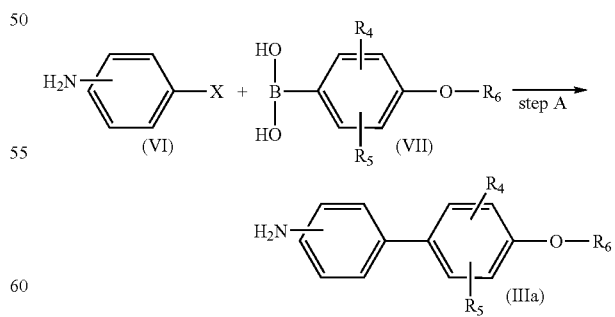

and one example of the cyclohexylidene series where A is cyclohexylidene yielding the non-aromatic amines of formula IIIb, also simulating saturated or unsaturated cyclic and heterocyclic bridge:

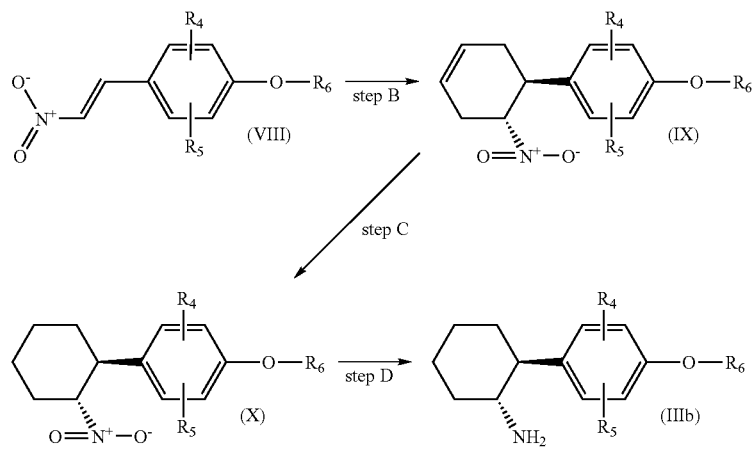

The compounds of formula III, in particular those of formulae IIIa and IIIb, have been created for the synthesis of the novel active ingredients of formula I. They constitute another feature of present invention.

Step A: The compounds of formula IIIa wherein $R_4$, $R_5$ and $R_6$ are as defined for formula I may be prepared by palladium-catalyzed cross-coupling reaction of an aryl boronic acid derivative of formula VII wherein $R_4$, $R_5$ and $R_6$ are as defined for formula I, with an aryl halide of formula VI wherein X is a halogen, preferentially bromine or iodine under the conditions of the Suzuki coupling, according to known procedures (Y. Miura et al., *Synthesis* 1995, 1419; M. Hird et al, *Synlett* 1999, 438).

Step B: A ω-nitrostyrene of formula VIII wherein $R_4$, $R_5$ and $R_6$ are as defined for formula I is heated in a Diels-Alder reaction (M. B. Smith and J. March, *Advanced Organic Chemistry*, 5$^{th}$ ed., Wiley, 2001, p. 1062) together with 1,3-butadiene to give a 4-nitro-5-aryl-cyclohexenyl derivative of formula IX, wherein $R_4$, $R_5$ and Re are as defined for formula I under conditions known per se (C. M. Nachtsheim and A. W. Frahm, *Arch. Pharm.* (*Weinheim*) 1989, 322, 187).

Step C: A 4-nitro-5-aryl-cyclohexenyl derivative of formula IX, wherein $R_4$, $R_5$ and $R_6$ are as defined for formula I is reduced to a 1-nitro-2-aryl-cyclohexyl derivative of formula X, wherein $R_4$, $R_5$ and $R_6$ are as defined for formula I. The reduction Is preferably performed by catalytic hydrogenation in the presence of a metal catalyst like palladium on carbon or palladium hydroxide on carbon at pressures ranging from 1 to 100 bar, preferentially at pressures ranging from 1 to 50 bar; and temperatures ranging from 0 to +150° C., preferentially at temperatures ranging from +20 to +100° C.

Step D: A 1-nitro-2-aryl-cyclohexyl derivative of formula X, wherein $R_4$, $R_5$ and $R_6$ are as defined for formula I is then further reduced to an 2-arylcyclohexylamine of formula IIIb, wherein $R_4$, $R_5$ and $R_6$ are as defined for formula I. The reduction is preferably performed in the presence of a reagent such as zinc, tin or iron, each of these metals together with a mineral acid like hydrochloric acid or sulfuric acid, indium together with ammonium chloride, hydrazine or hydrazine hydrate together with Raney-Nickel, sodium borohydride, lithium aluminum hydride or by catalytic hydrogenation in the presence of a catalyst such as platinum oxide at temperatures ranging from –80 to +200° C., preferentially at temperatures ranging from 40 to +120° C.

The compounds of formula I are oils or solids at room temperature and are distinguished by valuable microbiocidal properties. They can be used in the agricultural sector or related fields preventively and curatively in the control of plant-destructive microorganisms. The compounds of formula I according to the invention are distinguished at low rates of concentration not only by outstanding microbiocidal, especially fungicidal, activity but also by being especially well tolerated by plants.

Surprisingly, it has now been found that the compounds of formula I have for practical purposes a very advantageous biocidal spectrum in the control of phytopathogenic microorganisms, especially fungi. They possess very advantageous curative and preventive properties and are used in the protection of numerous crop plants. With the compounds of formula I it is possible to inhibit or destroy phytopathogenic microorganisms that occur on various crops of useful plants or on parts of such plants (fruit, blossom, leaves, stems, tubers, roots), while parts of the plants which grow later also remain protected, for example, against phytopathogenic fungi.

The novel compounds of formula I prove to be effective against specific genera of the fungus class Fungi imperfecti (e.g. *Cercospora*), Basidiomycetes (e.g. *Puccinia*) and Ascomycetes (e.g. *Erysiphe* and *Venturia*) and especially against Oomycetes (e.g. *Plasmo para*, *Peronospora*, *Pythium* and *Phytophthora*). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Also included is a method of protecting plants which comprises applying the novel compounds of formula I or the novel compositions to said plants.

Target crops to be protected within the scope of this invention include, for example, the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally used in the form of compositions and can be applied to the area or plant to be treated simultaneously or in succession with other active ingredients. Those other active ingredients may be fertilisers, micronutrient donors or other preparations that influence plant growth. It is also possible to use selective herbicides or insecticides, fungicides, bactericides, nematicides, molluscicides or mixtures of several of those preparations, if desired together with further carriers, surfactants or other application-promoting adjuvants customarily employed in formulation technology.

The compounds of formula I can be mixed with other fungicides, resulting in some cases in unexpected synergistic activities, e.g. synergistic enhancement of the biological effects. Preferred active ingredients advantageous as additives to the compositions comprising the active ingredient of formula I are: azoles, such as azaconazole, bitertanol, bromuconazole, cyproconazole, difenoconazole, diniconazole, epoxiconazole, fenbuconazole, fluquinconazole, flusilazole, flutriafol, hexaconazole, imazalil, S-imazalil, imibenconazole, ipconazole, metconazole, myclobutanil, oxpoconazole, pefurazoate, penconazole, pyrfenox, prochloraz, propiconazole, prothioconazole, simeconazole, tebuconazole, tetraconazole, triadimefon, triadimenol, triflumizole and tritconazole; pyrimidinyl carbinoles, such as ancymidol, fenarimol and nuarimol; 2-amino-pyrimidines, such as bupirimate, dimethirimol and ethirimol; morpholines, such as dodemorph, fenpropidine, fenpropimorph, spiroxamine and tridemorph; anilinopyrimidines, such as cyprodinil, mepanipyrim and pyrimethanil; pyrroles, such as fenpiclonil and fludioxonil; phenylamides, such as benalaxyl, furalaxyl, metalaxyl, R-metalaxyl, ofurace and oxadixyl; benzimidazoles, such as benomyl, carbendazim, debacarb, fuberndazole and thiabendazole; dicarboximides, such as chlozolinate, dichlozoline, iprodione, myclozoline, procymidone and vinclozoline; cartoxamides, such as carboxin, fenfuram, flutolanil, furametpyr, mepronil, oxycarboxin and thifluzamide; guanidines, such as guazatine, dodine and iminoctadine; strobilurines, such as azoxystrobin, dimoxystrobin (SSF-129), fluoxastrobin, kresoxim-methyl, metominostrobin, orysastrobin, picoxystrobin, pyraclostrobin and trifloxystrobin; dithiocarbamates, such as ferbam, mancozeb, maneb, metiram, propineb, thiram, zineb and ziram; N-halomethylthiotetrahydrophthalimides, such as captafol, captan, dichlofluanid, fluoromides, folpet and tolyfluanid; Copper-compounds, such as Bordeaux mixture, copper hydroxide, copper oxychloride, copper sulfate, cuprous oxide, mancopper and oxine-copper; nitrophenol-derivatives, such as dinocap and nitrothalisopropyl; organo-P-derivatives, such as edifenphos, iprobenphos, isoprothiolane, phosdiphen, pyrazophos and tolclofos-methyl; various others, such as acibenzolar-S-methyl, anilazine, benthiavalicarb, blasticidin-S, boscalid, chinomethionate, chloroneb, chlorothalonil, IKF-916 (proposed name cyazofamid), cyflufenamid, cymoxanil, dichione, diclomezine, dicloran, diethofencarb, dimethomorph, ethaboxam, fenoxanil, SYP-LI90 (proposed name: flumorph), dithianon, etridiazole, famoxadone, fenamidone, fentin, ferimzone, fluazinam, flusulfamide, fenhexamid, fosetyl-aluminium, hymexazol, iprovalicarb, kasugamycin, methasulfocarb, metrafenone, pencycuron, phthalide, picobenzamid, polyoxins, probenazole, propamocarb, pyroquilon, proquinazid, quinoxyfen, quintozene, silthiofam, sulfur, triazoxide, triadinil, tricyclazole, triforine, validamycin, or zoxamide.

Suitable carriers and surfactants may be solid or liquid and correspond to the substances ordinarily employed in formulation technology, such as e.g. natural or regenerated mineral substances, solvents, dispersants, wetting agents, tackifiers, thickeners, binders or fertilisers. Such carriers and additives are described, for example, in WO 95/30651.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to seed grains (coating) either by impregnating the grains with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the compound(s) (active ingredient(s)) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.01 to 99% by weight, preferably 0.1 to 95% by weight, of a compound of formula I, 99.99 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilisers or other active ingredients for obtaining special effects.

The following Examples illustrate the invention described above, without limiting the scope thereof in any way. Temperatures are given in degrees Celsius.

PREPARATION EXAMPLES FOR COMPOUNDS OF FORMULA I

Preparation-Example A1.1

2-(4-Chlorophenyl)-N-(3'-methoxy-4'-pent-2-yny-loxy-biphenyl-2-yl)-2-prop-2-ynyloxy-acetamide

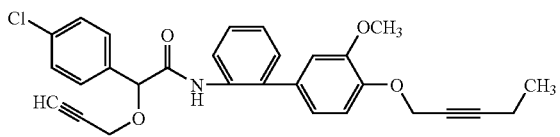

a) (4-Bromo-2-methoxy-phenoxy)-tert-butyl-diphenyl-silane

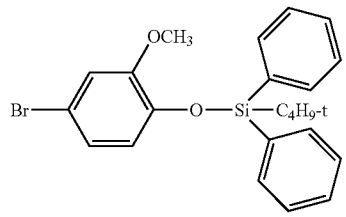

76.8 ml (300 mmol) tert-Butyldiphenylchlorosilane are added to a solution of 40.61 g (200 mmol) 4-bromoguaiacol and 27.23 g (400 mmol) imidazole in 200 ml dichloromethane at 0° C. The mixture is stirred for 4 hours at room temperature. The solution is diluted with CH$_2$Cl$_2$ and extracted with 300 ml water. The solvent of the organic phase is evaportated and the residue is purified by flash-chromatography (ethyl acetate/hexane 3:97), yieling (4-bromo-2-methoxy-phenoxy)-tert-butyl-diphenyl-silane as a colorless oil.

$^1$H-NMR (CDCl$_3$, 300 MHz): 1.15 (s, 9H, t-Bu), 3.55 (s, 3H, OMe), 6.55 (d, 1H, ar), 6.78 (2m, 1H, ar), 6.66 (s, 1H, ar), 7.3–7.5 (m, 6H, ar), 7.65–7.75 (m, 4H, ar).

b) 4-(tert-Butyl-diphenyl-silanyloxy)-3-methoxy-phenyl-boronic acid

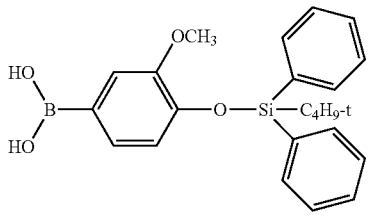

At −78° C., 140 ml n-BuLi (1.6 M in hexane, 223.8 mmol) in 600 ml THF are added to a solution of 89.92 g (203.4 mmol) (4-bromo-2-methoxy-phenoxy)-tert-butyl-diphenyl-silane over a period of 30 minutes. After further 30 minutes at −78° C., 140.9 ml (610.4 mmol) triisopropylborate are added over a period of 30 minutes. The mixture is allowed to warm up to room temperature and is then hydrolysed at 0° C. with a 10% HCl solution within 30 minutes. After separation of the water phase, the organic phase is dried over MgSO$_4$, condensed and the residue is crystallized-from ethyl acetate and a mixture of ethyl acetate/heptane, yielding. 4-(tert-butyl-diphenyl-silanyloxy)-3-methoxy-phenyl-boronic acid is isolated as a light yellow solid (m.p. 193–196° C.).

c) 4'-(tert-Butyl-diphenyl-silanyloxy)-3'-methoxy-biphenyl-2-ylamine

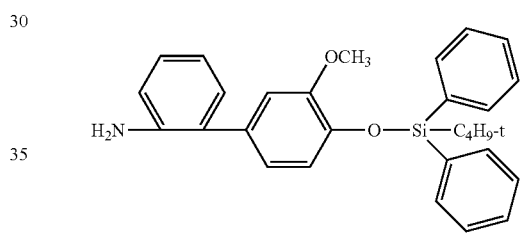

A solution of 17.89 g (44.0 mmol) 4-(tert-butyl-diphenyl-silanyloxy)-3-methoxy-phenyl-boronic acid, 6.89 g (31.45 mmol) 2-iodoaniline, 17.4 g (125.8 mmol) K$_2$CO$_3$ and 425 mg (6 mol %) Pd(OAc)$_2$ in 140 ml THF and 80 ml H$_2$O is heated to reflux for 20 hours. After cooling the mixture is filtrated over cellite and concentrated. The residue is dissolved in ethyl acetate and washed with water. After drying (MgSO$_4$) and evaporating the solvent, the residue is subjected to flash-chromatography (ethyl acetate/hexane 1:9). Yield: 4'-(tert-Butyl-diphenyl-silanyloxy)-3'-methoxy-biphenyl-2-ylamine is isolated as a colorless oil.

$^1$H-NMR (CDCl$_3$, 300 MHz): 1.15 (s, 9H, t-Bu), 3.55 (s, 3H, OMe), 6.6–6.9 (m, 5H, ar), 7.05–7.15 (m, 2H, ar), 7.30–7.50 (m, 6H, ar), 7.75 (m, 4H, ar).

d) N-[4'-(tert-Butyl-diphenyl-silanyloxy-3'-methoxy-biphenyl-2yl]-2-(4-chloro-phenyl]-2-prop-2-ynyloxy-acetamide

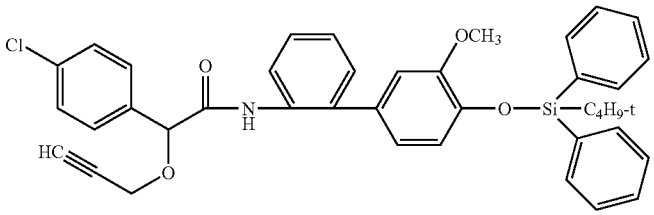

Oxalyl chloride (4.3 g, 33 mmol) is added to a solution of (4-chlorophenyl-prop-2-ynyloxy-acetic acid (6.8 g, 30 mmol) in a mixture of 150 ml of dichloromethane and few drops of N,N-dimethylformamide. The reaction mixture is stirred for 4 hours at room temperature and then added to a solution of 4'-(tert-butyl-diphenyl-silanyloxy)-3'-methoxy-biphenyl-2-ylamine (13.8 g, 30 mmol) and triethylamine (4.6 g, 45 mmol) in 150 ml of dichloromethane. The resulting mixture is stirred for 16 hours at room temperature under a nitrogen atmosphere. Subsequently, the mixture is diluted with chloroform and extracted with water. The combined organic layer is dried over sodium sulfate and evaporated and the remaining crude product is subjected to flash-chromatography (ethyl acetate/hexane 3;7) yielding N-[4'-(tert-butyl-diphenyl-silanyloxy)-3'-methoxy-biphenyl-2-yl]-2-(4-chlorophenyl)-2-prop-2-ynyloxy-acetamide as an orange oil.

$^1$H-NMR (CDCl$_3$, 300 MHz); 1.15 (s, 9H, t-Bu), 2.39 (t, 1H, C≡CH), 3.61 (s, 3H, OMe), 3.80 (dd, 1H, CH$_2$C≡C), 3.92 (dd, 1H, CH$_2$C≡C), 4.99 (s, 1H), 6.63–8.72 (m, 22H, ar, NH).

e) 2-(4–Chlorophenyl)-N-(4'-hydroxy-3'-methoxy-biphenyl-2-yl)-2-prop-2-ynyloxy-acetamide

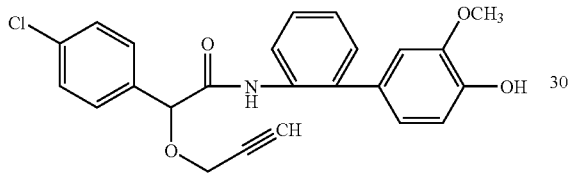

A solution of 10.2 g (15.5 mmol) N-[4'-(tert-butyl-diphenyl-silanyloxy)-3'-methoxy-biphenyl-2-yl]-2-(4-chlorophenyl)-2-prop-2-ynyloxy-acetamide and 24.5 g (77.5 mmol) tetrabutylammonium fluoride in 200 ml of dichloromethane is stirred for 4 hours at room temperature. After extracting with water/ethyl acetate and evaporation of the organic phase, the residue is subjected to flash-chromatography (ethyl acetate/hexane 4:6). Yield: 2-(4-chlorophenyl)-N-(4'-hydroxy-3'-methoxy-biphenyl-2-yl)-2-prop-2-ynyloxy-acetamide, m.p. 140–142° C.

$^1$H-NMR (CDCl$_3$, 300 MHz): 2.48 (t, 1H, C≡CH), 3.89 (s, 3H, OMe), 3.93 (dd, 1H, CH$_2$C≡C), 4.10 (dd, 1H, CH$_2$C—C), 5.03 (s, 1H), 6.84–8.22 (m, 12H, ar, NH).

f) A solution of 1.3 g (3.1 mmol) 2-(4-chloro-phenyl)-N-(4'-hydroxy-3'-methoxy-biphenyl-2-yl)-2-prop-2-ynyloxy-acetamide, 6.0 ml (6.0 mmol) of a 1 M solution of sodium methoxide in methanol and 0.5 g (4.7 mmol) 2-pentynyl chloride in 50 ml of methanol is heated to reflux for 3 hours. After cooling, the reaction mixture is poured into ethyl acetate. The organic layer is washed with brine, dried over sodium sulfate and evaporated. The remaining product is subjected to flash-chromatography (ethyl acetate/hexane 4:6) to yield 2-(4-chlorophenyl)-N-(3'-methoxy-4'-pent-2-ynyloxy-biphenyl-2-yl)-2-prop-2-ynyloxy-acetamide as yellow oil.

$^1$H-NMR (CDCl$_3$, 300 MHz): 1.13 (t, 3H, Me), 2.22 (q, 2H, CH$_2$), 2.50 (t, 1H, C≡CH), 3.88 (s, 3H, OMe), 3.95 (d, 1H, —CH$_2$C≡C ), 4.07 (d, 1H, CH$_2$C≡C), 4.82 (d, 2H, CH$_2$), 5.04 (s, 1H), 6.88–8.78 (m, 12H, ar, NH).

According to the Preparation-Example A1.1 described above the compounds of formula I may be obtained.

Example A1.2

2-(3,4-Dichlorophenyl)-N-[trans-2-(3-methoxy-4-prop-2-ynyloxy-phenyl)-cyclohexyl]-2-prop-2-ynyloxy-acetamide

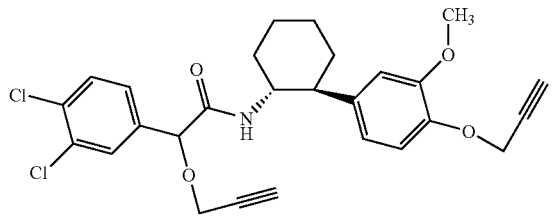

a) trans-2-Methoxy-4-(6-nitro-cyclohex-3-enyl)-phenol

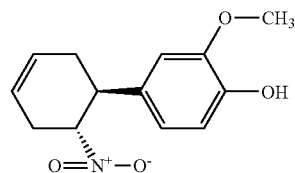

A mixture of 50 g of 3-methoxy-4-hydroxy-ω-nitrostyrene, 1.0 g (9.1 mmol) of hydrochinone and 55 g (1.02 mol) of 1,3-butadiene in 200 ml toluene is made at −78° C. This mixture is stirred at +130° C. for 4 days in an autoclave. Subsequently, the toluene is evaporated in vacuum. The dark brown oil is purified by crystallization from ethanol. This method allows to obtain trans-2-methoxy-4-(6-nitro-cyclohex-3-enyl)-phenol.

$^1$H-NMR (CDCl$_3$, 300 MHz): 2.28–2.83 (m, 4H, CH$_2$), 3.34 (td, 1H), 3.87 (s, 3H, OCH$_3$), 4.89 (td, 1H), 5.53 (s, 1H, OH), 5.71–5.84 (m, 2H, CH═CH), 6.69 (d, 1H, ar), 6.73 (dd, 1H, ar), 6.85 (d, 1H, ar).

b) trans-2-Methoxy-4-(2-nitro-cyclohexyl)-phenol

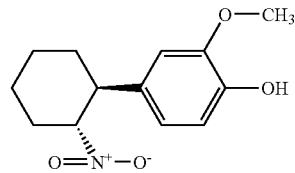

1in 300 ml methanol 8.4 g (33.7 mmol) of trans-2-methoxy-4-(6-nitro-cyclohex-3-enyl)-phenol are solved. To this solution 500 mg of 10% Pd/C are added. The mixture is hydrogenated at room temperature for 6 hours. The mixture was then filtered through Filter Cel and evaporation of the filtrate in vacuum, yielding trans-2 methoxy-4-(2-nitro-cyclohexyl)-phenol as a light yellow solid.

$^1$H-NMR (CDCl$_3$. 300 MHz): 1.40–2.40 (m, 8H, CH$_2$), 3.05 (td, 1H), 3.85 (s, 3H, OCH$_3$), 4.62 (td, 1H), 6.65 (d, 1H, ar), 6.69 (dd, 1H, ar), 6.83 (d, 1H, ar).

c) trans-4-(2-Amino-cyclohexyl)-2-methoxy-phenol

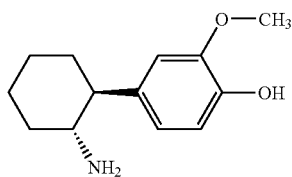

A solution of 8.5 g (33.8 mmol) of trans-2-methoxy-4-(2-nitro-cyclohexyl)-phenol is prepared in 300 ml methanol. To this are added simultaneously 7 ml of hydrazine hydrate and 2.5 g of Raney-Nickel over 8 hours with vigorous stirring. Upon completion of the addition the reaction mixture is stirred for another 16 hour at room temperature. The mixture is then filtered and evaporation of the filtrate in vacuum gives trans-4-(2-amino-cyclohexyl)-2-methoxy-phenol as a light yellow solid.

$^1$H-NMR (CDCl$_3$, 300 MHz): 1.20–2.10 (m, 8H, CH2), 2.17 (td, 1H), 2.77 (td, 1H), 3.87 (s, 3H, OCH3), 6.72 (d, 1H, ar), 6.79 (dd, 1H, ar), 6.89 (d, 1H, ar).

d) 2-(3,4-Dichlorophenyl)-2-hydroxy-N-[trans-2-(4-hydroxy-3-methoxy-phenyl)-cyclohexyl]-acetamide

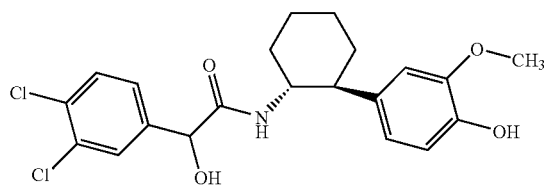

To a stirred solution of 3.09 g (13.5 mmol) of DL-3,4-dichloromandelic acid, 3.0 g (13.5 mmol) of trans-4-(2-amino-cyclohexyl)-2-methoxy-phenol and 1.89 (13.5 mmol) of N,N-diisopropylethylamine in 30 ml DMF is added 6.0 g (13.5 mmol) of benzotriazol-1-yloxytris(dimethylamino)phosphonium hexafluorophosphate in one portion. The reaction mixture is then stirred at ambient temperature for about 2 hours and thereafter poured into 150 ml of aqueous saturated sodium chloride solution. The two-phase mixture is extracted with two 150 ml portions of ethyl acetate. The organic extract is concentrated under reduced pressure to a residue, which is subjected to column chromatography on silica gel, with 1:1 ethyl acetate/isohexane as the eluant yielding 2-(3,4-dichlorophenyl)-2-hydroxy-N-[trans-2-(4-hydroxy-3-methoxy-phenyl)-cyclohexyl]-acetamide.

$^1$H-NMR (CDCl$_3$, 300 MHz): 1.17–2.24 (m, 10H), 3.76 (s, 3H, OCH$_3$), 3.93 (m, 1H), 4.67 (s, 1H), 5.42 (d, 2H), 6.47–7.21 (m, 6H, ar).

e) 2-(3,4-Dichlorophenyl)-2-hydroxy-N-[trans-2-(3-methoxy-4-prop-2-ynyloxy-phenyl-cyclohexyl]-acetamide

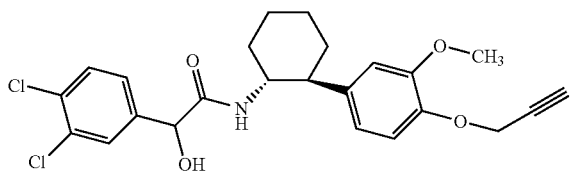

A solution of 0.6 g (1.4 mmol) of 2-(3,4-dichlorophenyl)-2-hydroxy-N-[trans-2-(4-hydroxy-3-methoxy-phenyl)-cyclohexyl]-acetamide and 0.4 g (1.9 mmol) of propynyl tosylate and 2.7 ml of 1 M solution of sodium methoxide in 10 ml methanol is heated to reflux for 3 hours. The reaction mixture is cooled and poured into 30 ml of aqueous saturated sodium chloride solution and finally extracted with two 100 ml portions of ethyl acetate. The combined organic extract is concentrated under reduced pressure to a residue, which is subjected to column chromatography on silica gel, with 1:1 ethyl acetate/isohexane as the eluant to obtain 2-(3,4-dichlorophenyl)-2-hydroxy-N-[trans-2-(3-methoxy-4-prop-2-ynyloxy-phenyl)-cyclohexyl]-acetamide.

$^1$H-NMR (CDCl$_3$, 300 MHz): 1.20–2.21 (m, 8H), 2.23 (td, 1H), 2.51 (t, 1H, C≡CH), 3.75 (bs, 1H, OH), 3.79 (s, 3H, OCH$_3$), 4.01 (m, 1H), 4.70 (s, 1H), 4.76 (d, 2H, CH$_2$C≡C), 5.42 (d, 1H), 6.54–7.26 (m, 6H, ar).

f) To a stirred solution of 0.4 g (0.85 mmol) of 2-(3,4-dichlorophenyl)-2-hydroxy-N-[trans-2-(3-methoxy-4-prop-2-ynyloxy-phenyl)-cyclohexyl]-acetamide, 0.5 ml of 30% aqueous sodium hydroxide solution and 5 mg of tetrabutylammonium bromide in 3 ml dichloromethane is added 0.18 g (0.85 mmol) of propynyl tosylate during 1 hour. Upon completion of the addition the reaction mixture is stirred for additional 16 hours at room temperature. The mixture is then extracted with dichloromethane. The organic extract is concentrated under reduced pressure to a residue, which was subjected to column chromatography on silica gel, with 1:2 ethyl acetate/isohexane as the eluant to obtain 2-(3,4-dichlorophenyl)-N-[trans-2-(3-methoxy-4-prop-2-ynyloxy-phenyl)-cyclohexyl]-2-prop-2-ynyloxy-acetamide.

$^1$H-NMR (CDCl$_3$, 300 MHz): 1.23–2.10 (m, 8H), 2.37 (td, 1H), 2.43 (t, 1H, C≡CH), 2.49 (t, 1H, C≡CH), 3.68 (d, 2H), 3.87 (s, 3H, OCH$_3$), 3.97 (m, 1H), 4.62 (s, 1H), 4.74 (d, 2H, CH$_2$C≡C), 6.32 (d, 1H, —NH), 6.75–7.43 (m, 6H, ar).

According to the example A1.2 described above the compounds listed in table A2 are obtained.

TABLE A2

| No. | $R_1$ | $R_3$ | $R_6$ | physico-chemical data |
|---|---|---|---|---|
| A2.03 | H | 4-Br—Ph | —CH$_2$—C≡CH | m.p. 158–159 |
| A2.05 | —CH$_2$—C≡CH | 4-Cl—Ph | —CH$_2$—C≡CH | m.p. 123–125 |
| A2.06 | —CH$_2$—C≡CH | 4-Br—Ph | —CH$_2$—C≡CH | m.p. 140–142 |
| A2.07 | —CH$_2$—C≡CH | 3,4-Cl$_2$—Ph | —CH$_2$—C≡CH | m.p. 124–126 |
| A2.09 | H | 4-Cl—Ph | —CH$_2$—C≡CH | m.p. 144–146 |
| A2.11 | H | 3,4-Cl$_2$—Ph | —CH$_2$—C≡CH | m.p. 127–129 |

Analogously to the above Examples the following compounds of Tables 1 to 50 may be prepared. In the tables Ph means phenyl.

Table 2: Compounds represented by the Formula I.02 wherein the combination of the groups $R_1$, $R_4$, $R_5$ and $R_6$ corresponds to each row in table A.

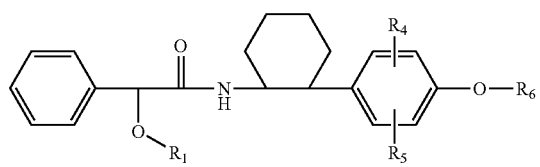
(I.02)

Table 4: Compounds represented by the Formula I.04 wherein the combination of the groups $R_1$, $R_4$, $R_5$, $R_6$ corresponds to each row in table A.

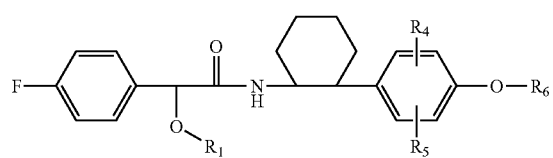
(I.04)

Table 6: Compounds represented by the Formula I.06 wherein the combination of the groups $R_1$, $R_4$, $R_5$, $R_6$ corresponds to each row in table A.

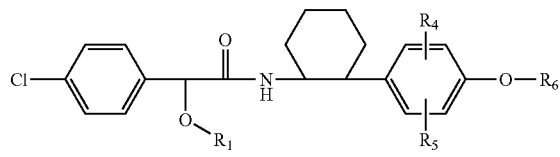
(I.06)

Table 8: Compounds represented by the Formula I.08 wherein the combination of the groups $R_1$, $R_4$, $R_5$, $R_6$ corresponds to each row in table A.

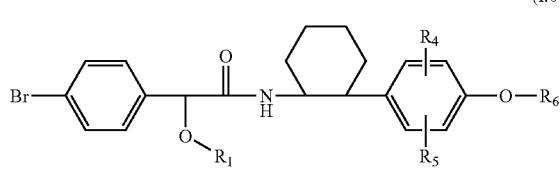
(I.08)

Table 10: Compounds represented by the Formula I.10 wherein the combination of the groups $R_1$, $R_4$, $R_5$ and $R_6$ corresponds to each row in table A.

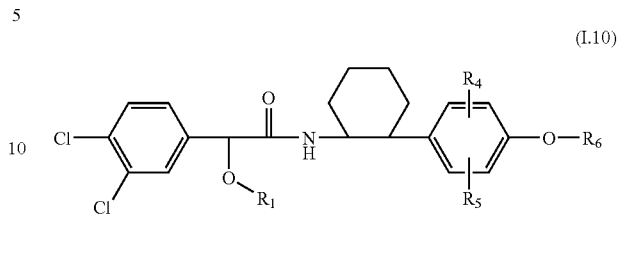
(I.10)

Table 12: Compounds represented by the Formula I.12 wherein the combination of the groups $R_1$, $R_4$, $R_5$ and $R_6$ corresponds to each row in table A.

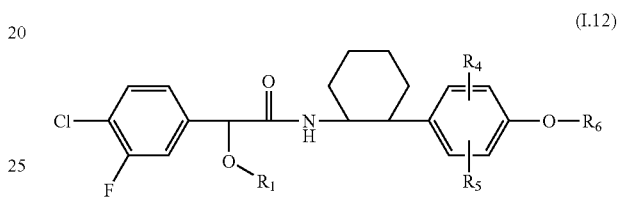
(I.12)

Table 14: Compounds represented by the Formula I.14 wherein the combination of the groups $R_1$, $R_4$, $R_5$ and $R_6$ corresponds to each row in table A.

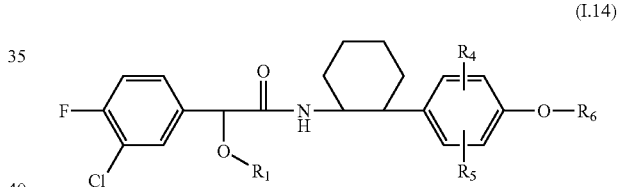
(I.14)

Table 16: Compounds represented by the Formula I.16 wherein the combination of the groups $R_1$, $R_4$, $R_5$ and $R_6$ corresponds to each row in table A.

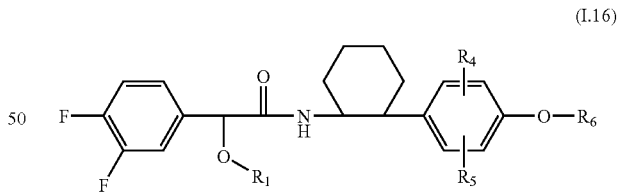
(I.16)

Table 18: Compounds represented by the Formula I.18 wherein the combination of the groups $R_1$, $R_4$, $R_5$ and $R_6$ corresponds to each row in table A.

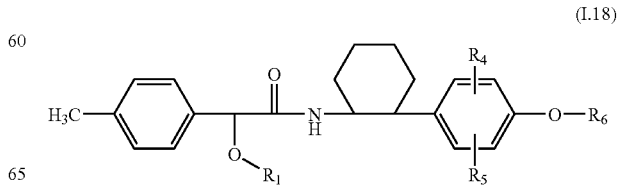
(I.18)

Table 20: Compounds represented by the Formula I.20 wherein the combinations of the groups $R_1$, $R_4$, $R_5$ and $R_6$ corresponds to each row in table A.

(I.20)

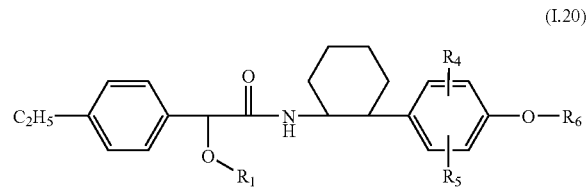

Table 22: Compounds represented by the Formula I.22 wherein the combination of the groups $R_1$, $R_4$, $R_5$ and $R_6$ corresponds to each row in table A.

(I.22)

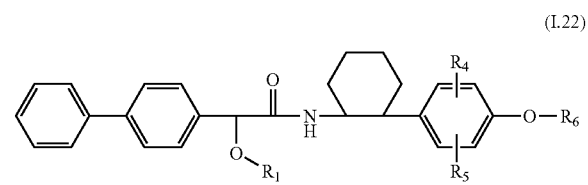

Table 24: Compounds represented by the Formula I.24 wherein the combination of the groups $R_1$, $R_4$, $R_5$ and $R_6$ corresponds to each row in table A.

(I.24)

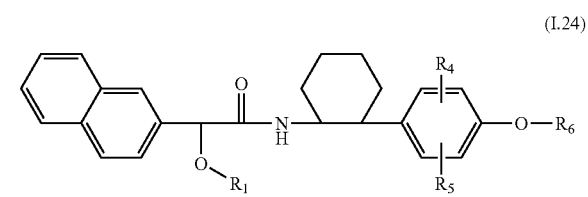

Table 26: Compounds represented by the Formula I.26 wherein the combination of the groups $R_1$, $R_4$, $R_5$ and $R_6$ corresponds to each row in table A.

(I.26)

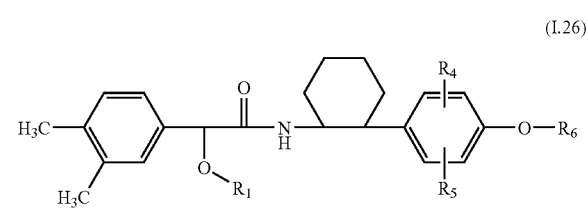

Table 28: Compounds represented by the Formula I.28 wherein the combination of the groups $R_1$, $R_4$, $R_5$ and $R_6$ corresponds to each row in table A.

(I.28)

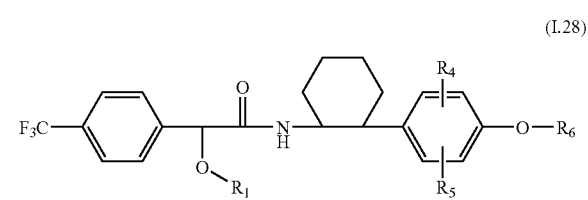

Table 30: Compounds represented by the Formula I.30 wherein the combination of the groups $R_1$, $R_4$, $R_5$ and $R_6$ corresponds to each row in table A.

(I.30)

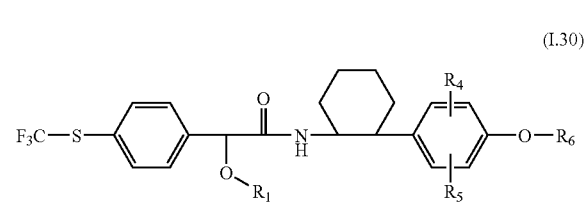

Table 32: Compounds represented by the Formula I.32 wherein the combination of the groups $R_1$, $R_4$, $R_5$ and $R_6$ corresponds to each row in Table A.

(I.32)

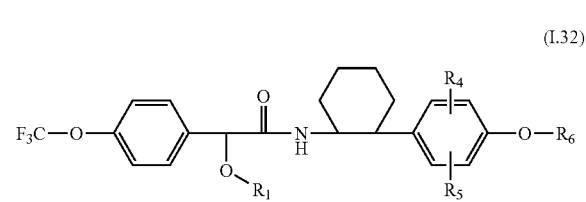

Table 34: Compounds represented by the Formula I.34 wherein the combination of the groups $R_1$, $R_4$, $R_5$ and $R_6$ corresponds to each row in table A.

(I.34)

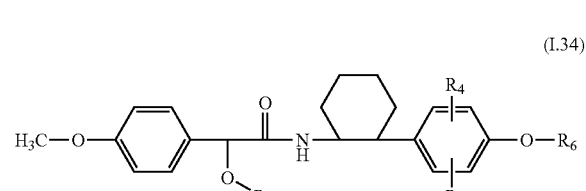

Table 36: Compounds represented by the Formula I.36 wherein the combination of the groups $R_1$, $R_4$, $R_5$ and $R_6$ corresponds to each row in table A.

(I.36)

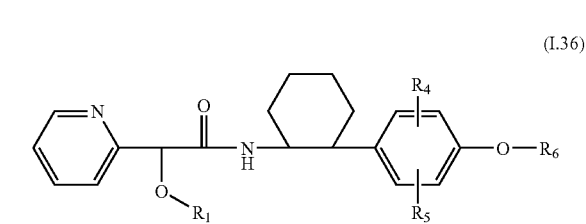

Table 38: Compounds represented by the Formula I.38 wherein the combination of the groups $R_1$, $R_4$, $R_5$ and $R_6$ corresponds to each row in table A.

(I.38)

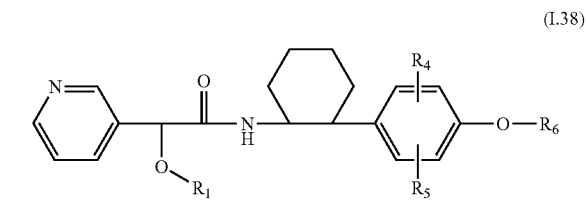

Table 40: Compounds represented by the Formula I.40 wherein the combination of the groups $R_1$, $R_4$, $R_5$ and $R_6$ corresponds to each row in table A.

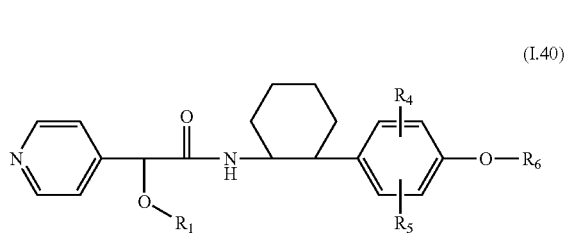
(I.40)

Table 42: Compounds represented by the Formula I.42 wherein the combination of the groups $R_1$, $R_4$, $R_5$ and $R_6$ corresponds to each row in table A.

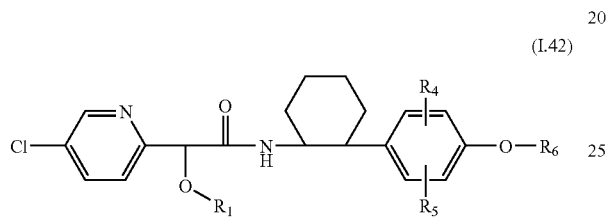
(I.42)

Table 44: Compounds represented by the Formula I.44 wherein the combination of the groups $R_1$, $R_4$, $R_5$ and $R_6$ corresponds to each row in table A.

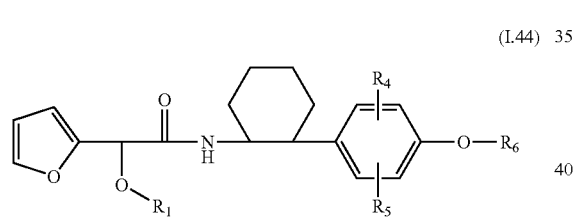
(I.44)

Table 46: Compounds represented by the Formula I.46 wherein the combination of the groups $R_1$, $R_4$, $R_5$ and $R_6$ corresponds to each row in table A.

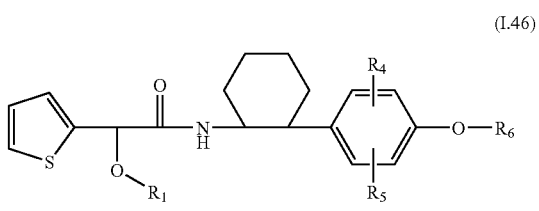
(I.46)

Table 48: Compounds represented by the Formula I.48 wherein the combination of the groups $R_1$, $R_4$, $R_5$ and $R_6$ corresponds to each row in table A.

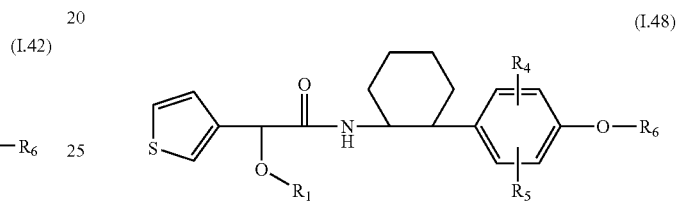
(I.48)

Table 50: Compounds represented by the Formula I.50 wherein the combination of the groups $R_1$, $R_4$, $R_5$ and $R_6$ corresponds to each row in table A.

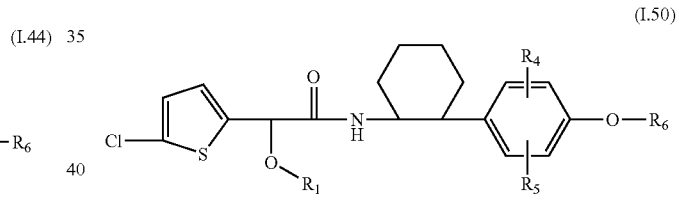
(I.50)

In table A the designation Ph stands for phenyl.

TABLE A

| No. | $R_1$ | $R_4$ | $R_5$ | $R_6$ |
|---|---|---|---|---|
| 009 | H— | H— | H— | —$CH_2$—C≡CH |
| 024 | $CH_3$— | H— | H— | —$CH_2$—C≡CH |
| 039 | $CH_3$—$CH_2$— | H— | H— | —$CH_2$—C≡CH |
| 054 | HC≡$CCH_2$— | H— | H— | —$CH_2$—C≡CH |
| 071 | H— | 3-$CH_3$—O— | H— | —$CH_2$—C≡CH |
| 096 | $CH_3$— | 3-$CH_3$—O— | H— | —$CH_2$—C≡CH |
| 121 | $CH_3$—$CH_2$— | 3-$CH_3$—O— | H— | —$CH_2$—C≡CH |
| 146 | HC≡$CCH_2$— | 3-$CH_3$—O— | H— | —$CH_2$—C≡CH |
| 164 | $H_3$CC≡$CCH_2$— | 3-$CH_3$—O— | H— | —$CH_2$—C≡CH |
| 174 | $CH_2F$— | 3-$CH_3$—O— | H— | —$CH_2$—C≡CH |
| 179 | $CHF_2$— | 3-$CH_3$—O— | H— | —$CH_2$—C≡CH |
| 184 | $CF_3$— | 3-$CH_3$—O— | H— | —$CH_2$—C≡CH |
| 189 | $CH_3$—$CH_2$— | 3-$CH_3$—O— | H— | —$CH_2$—C≡CH |

TABLE A-continued

| No. | $R_1$ | $R_4$ | $R_5$ | $R_6$ |
|---|---|---|---|---|
| 194 | $CH_3CH_2CH_2$— | 3-$CH_3$—O— | H— | —$CH_2$—C≡CH |
| 199 | $(CH_3)_2CH$— | 3-$CH_3$—O— | H— | —$CH_2$—C≡CH |
| 204 | H— | 3-$CH_3$—$CH_2$—O— | H— | —$CH_2$—C≡CH |
| 209 | $CH_3$— | 3-$CH_3$—$CH_2$—O— | H— | —$CH_2$—C≡CH |
| 214 | $CH_3CH_2$— | 3-$CH_3$—$CH_2$—O— | H— | —$CH_2$—C≡CH |
| 219 | HC≡$CCH_2$— | 3-$CH_3$—$CH_2$—O— | H— | —$CH_2$—C≡CH |
| 224 | H— | 3-$CH_3$— | H— | —$CH_2$—C≡CH |
| 229 | $CH_3$— | 3-$CH_3$— | H— | —$CH_2$—C≡CH |
| 234 | $CH_3CH_2$— | 3-$CH_3$— | H— | —$CH_2$—C≡CH |
| 239 | HC≡$CCH_2$— | 3-$CH_3$— | H— | —$CH_2$—C≡CH |
| 244 | H— | 3-Cl— | H— | —$CH_2$—C≡CH |
| 249 | $CH_3$— | 3-Cl— | H— | —$CH_2$—C≡CH |
| 254 | $CH_3CH_2$— | 3-Cl— | H— | —$CH_2$—C≡CH |
| 259 | HC≡$CCH_2$— | 3-Cl— | H— | —$CH_2$—C≡CH |
| 264 | H— | 3-Br— | H— | —$CH_2$—C≡CH |
| 269 | $CH_3$— | 3-Br— | H— | —$CH_2$—C≡CH |
| 274 | $CH_3CH_2$— | 3-Br— | H— | —$CH_2$—C≡CH |
| 279 | HC≡$CCH_2$— | 3-Br— | H— | —$CH_2$—C≡CH |
| 284 | H— | 3-$CH_3$—O— | 5-$CH_3$—O— | —$CH_2$—C≡CH |
| 289 | $CH_3$— | 3-$CH_3$—O— | 5-$CH_3$—O— | —$CH_2$—C≡CH |
| 294 | $CH_3CH_2$— | 3-$CH_3$—O— | 5-$CH_3$—O— | —$CH_2$—C≡CH |
| 299 | HC≡$CCH_2$— | 3-$CH_3$—O— | 5-$CH_3$—O— | —$CH_2$—C≡CH |

Formulations may be prepared analogously to those described in, for example, WO95/30651.

BIOLOGICAL EXAMPLES

D-1: Action against *Plasmopara viticola* (Downy Mildew) on Vines 5 week old grape seedlings cv. Gutedel are treated with the formulated test compound in a spray chamber. One day after application grape plants are inoculated by spraying a sporangia suspension ($4 \times 10^4$ sporangia/ml) on the lower leaf side of the test plants. After an incubation period of 6 days at +21° C. and 95% r. h. in a greenhouse the disease incidence is assessed.

Compounds of Tables 1 to 44 exhibit a good fungicidal action against *Plasmopara viticola* on vines. Compounds 6.071, 6.146, 8.146, and 10.146 at 200 ppm inhibit fungal infestation in this test to at least 800/eq while under the same conditions untreated control plants are infected by the phytopathogenic fungi to over 80%.

D-2: Action against Phytophthora (Late Blight) on Tomato Plants 3 week old tomato plants cv. Roter Gnom are treated with the formulated test compound in a spray chamber. Two day after application the plants are inoculated by spraying a sporangia suspension ($2 \times 10^4$ sporangia/ml) on the test plants. After an incubation period of 4 days at +18° C. and 95% r. h. in a growth chamber the disease incidence is assessed. Compounds of Tables 1 to 44 exhibit a long-lasting effect against fungus infestation. Compounds 6.071, 6.146, 8.146, and 10.146 at 200 ppm inhibit fungal infestation in this test to at least 80%, while under the same conditions untreated control plants are infected by the phytopathogenic fungi to over 80%.

D-3 Action against Phytophthora (Late Blight) on Potato Plants 5 week old potato plants cv. Bintje are treated with the formulated test compound in a spray chamber. Two day after application the plants are inoculated by spraying a sporangia suspension ($14 \times 10^4$ sporangia/ml) on the test plants. After an incubation period of 4 days at +18° C. and 95% r. h. in a growth chamber the disease incidence is assessed. Fungal infestation is effectively controlled with compounds of Tables 1 to 44.

Compounds 6.146, and 8.146 at 200 ppm inhibit fungal infestation in this test to at least 80%, while under the same conditions untreated control plants are infected by the phytopathogenic fungi to over 80%.

What is claimed is:

1. N-aryl-cycloalkylidenyl-α-hydroxy- and α-alkoxy acetic acid amides of the general formula I (I)

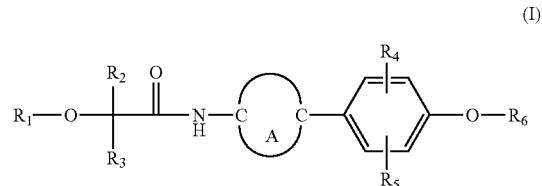

including the optical isomers thereof and mixtures of such isomers, wherein
$R_1$ is hydrogen, $C_1$–$C_{12}$alkyl; $C_2$–$C_{12}$alkenyl; $C_2$–$C_{12}$alkynyl; or $C_1$–$C_{12}$haloalkyl;
$R_2$ is hydrogen; $C_1$–$C_4$alkyl; $C_1$–$C_4$haloalkyl; $C_2$–$C_5$alkenyl or $C_2$–$C_5$alkynyl;
$R_3$ is aryl or heteroaryl, each optionally substituted with substituents selected from the group consisting of C$_1$–C$_8$alkyl, C$_2$–C$_8$alkenyl, C$_2$–C$_8$alkynyl, C$_3$–C$_8$cycloalkyl, C$_3$–C$_8$cycloalkyl-C$_1$–C$_4$alkyl, phenyl and phenylC$_1$–C$_4$alkyl, where all these groups may be substituted with one or more halogen atoms; C$_1$–C$_8$alkoxy, C$_3$–C$_8$alkenyloxy; C$_3$–C$_8$alkynyloxy; C$_1$–C$_8$alkoxy-C$_1$–C$_4$alkyl; C$_1$–C$_8$haloalkyl, C$_1$–C$_8$alkylthio; C$_1$–C$_8$haloalkylthio; C$_1$–C$_8$alkylsulfonyl; formyl; C$_1$–C$_8$alkanoyl; hydroxy; cyano; nitro; amino; C$_1$–C$_8$alkylamino; C$_1$–C$_8$dialkylamino; carboxyl; C$_1$–C$_8$alkoxycarbonyl; C$_3$–C$_8$alkenyloxycarbonyl and C$_3$–C$_8$alkynyloxycarbonyl; or A is a 1,2-cyclohexylidene or 1,2-cyclopropylidene bridge, R$_4$ is hydrogen C$_1$–C$_8$alkyl; C$_2$–C$_8$alkenyl; C$_2$–C$_8$alkynyl; C$_3$–C$_8$cycloalkyl; C$_3$–C$_8$cycloalkyl-C$_1$–C$_4$alkyl; C$_1$–C$_8$alkylthio; C$_1$–C$_8$alkylsulfonyl; C$_1$–C$_8$alkoxy; C$_3$–C$_8$alkenyloxy; C$_3$–C$_8$alkynyloxy; C$_3$–C$_8$cycloalkoxy; C$_1$–C$_8$alkoxy-C$_1$–C$_4$alkyl; C$_1$–C$_8$alkoxycarbonyl; C$_3$–C$_8$alkenyloxycarbonyl; C$_3$–C$_8$alkynyloxycarbonyl; C$_1$–C$_8$alkanoyl; C$_1$–C$_8$dialkylamino or C$_1$–C$_8$alkylamino, wherein in turn the alkyl, alkenyl, alkynyl or cycloalkyl moieties may be partially or fully halogenated; or is carboxyl; formyl; halogen; nitro; cyano; hydroxy or amino; and R$_5$ is hydrogen; C$_1$–C$_8$alkyl; C$_2$–C$_8$alkenyl; C$_2$–C$_8$alkynyl; C$_3$–C$_8$cycloalkyl; C$_3$–C$_8$cycloalkyl-C$_1$–C$_4$alkyl; C$_1$–C$_8$alkylthio; C$_1$–C$_8$alkylsulfonyl; C$_1$–C$_8$alkoxy; C$_3$–C$_8$alkenyloxy; C$_3$–C$_8$alkynyloxy; C$_3$–C$_8$cycloalkoxy; C$_1$–C$_8$alkoxy-C$_1$–C$_4$alkyl; C$_1$–C$_8$alkoxycarbonyl; C$_3$–C$_8$alkenyloxycarbonyl; C$_3$–C$_8$alkynyloxycarbonyl; C$_1$–C$_8$alkanoyl; C$_1$–C$_8$dialkylamino or C$_1$–C$_8$alkylamino, wherein in turn the alkyl, alkenyl, alkynyl or cycloalkyl moieties may be partially or fully halogenated; or is carboxyl; formyl; halogen; nitro; cyano; hydroxy or amino; and R$_6$ is propargyl.

2. A compound according to claim 1 wherein R$_2$ is hydrogen.

3. A compound according to claim 1, wherein R$_4$ is hydrogen; C$_1$–C$_8$alkyl; C$_1$–C$_8$haloalkyl; C$_2$–C$_8$alkenyl; C$_2$–C$_8$alkynyl; C$_1$–C$_8$alkylthio; C$_1$–C$_8$haloalkylthio; C$_1$–C$_8$alkoxy; C$_1$–C$_8$haloalkoxy; C$_1$–C$_8$alkoxy-C$_1$–C$_4$alkyl; C$_1$–C$_8$alkoxycarbonyl; C$_1$–C$_8$alkanoyl; formyl; halogen; nitro; cyano or hydroxy; and R$_5$ is hydrogen; C$_1$–C$_4$alkyl; C$_1$–C$_4$haloalkyl; C$_1$–C$_4$alkoxy; C$_1$–C$_4$alkoxycarbonyl; C$_1$–C$_4$alkanoyl; formyl; halogen; cyano or hydroxy; and R$_6$ is propargyl.

4. A compound according to claim 1, wherein R$_1$ is hydrogen, C$_1$–C$_4$alkyl, or C$_2$–C$_5$alkynyl; and R$_2$ is hydrogen and R$_3$ is phenyl or phenyl substituted with 1 to 3 substituents selected from C$_1$–C$_8$alkyl, C$_2$–C$_8$alkenyl, C$_3$–C$_8$cycloalkyl, C$_1$–C$_8$alkylthio, C$_1$–C$_8$alkoxycarbonyl, C$_1$–C$_8$haloalkyl, C$_1$–C$_8$haloalkoxy, C$_1$–C$_8$haloalkylthio, halogen, nitro or cyano; and A is 1,2-cyclohexylidene or 1,2-cyclopropylidene, and R$_4$ is hydrogen; C$_1$–C$_4$alkyl; C$_1$–C$_4$alkoxy; C$_1$–C$_4$haloalkoxy or halogen; and R$_5$ is hydrogen; C$_1$–C$_4$alkyl; halogen or cyano; and R$_6$ is propargyl.

5. A compound according to claim 1, wherein R$_1$ is hydrogen or C$_2$–C$_5$alkynyl; and R$_2$ is hydrogen and R$_3$ is phenyl; C$_{1-4}$alkylphenyl or halophenyl; and A is 1,2-cyclohexylidene or 1,2-cyclopropylidene; and R$_4$ is hydrogen; methoxy or ethoxy; and R$_5$ is hydrogen; and R$_6$ is propargyl.

6. A compound according to claim 1, wherein R$_1$ is hydrogen or propargyl; and R$_2$ is hydrogen; and R$_3$ is phenyl optionally substituted by one to two substituents selected from the group comprising methyl, ethyl, methoxy, fluoro, chloro, bromo, phenyl, trifluoromethyl, trifluoromethylthio or trifluoromethoxy; and A is 1,2-cyclohexylidene; and R$_4$ is hydrogen or methoxy; and R$_5$ is hydrogen; and R$_6$ is propargyl.

7. A compound according to claim 1, wherein R$_1$ is propargyl; and R$_2$ is hydrogen; and R$_3$ is phenyl optionally substituted by one to two substituents selected from the group consisting of fluoro, chloro and bromo, or is phenyl optionally substituted by one substituent selected from the group comprising methyl, ethyl, methoxy, phenyl, trifluoromethyl, trifluoromethylthio and trifluoromethoxy; and A is 1,2-cyclohexylidene; and R$_4$ is hydrogen or methoxy; and R$_5$ is hydrogen; and R$_6$ is propargyl.

8. A compound according to claim 1 selected from the group consisting 2-hydroxy-N-[trans-2-(3-methoxy-4-prop-2-ynyloxy-phenyl)-cyclohexyl]-2-phenyl-acetamide, 2-(4-chlorophenyl)-2-hydroxy-N-[trans-2-(3-methoxy-4-prop-2-ynyloxy-phenyl)-cyclohexyl]-acetamide, 2-(4-bromophenyl)-2-hydroxy-N-[trans-2-(3-methoxy-4-prop-2-ynyloxy-phenyl)-cyclohexyl]-acetamide, 2-(3,4-dichlorophenyl)-2-hydroxy-N-[trans-2-(3-methoxy-4-prop-2-ynyloxy-phenyl)-cyclohexyl]-acetamide, N-[trans-2-(3-methoxy-4-prop-2-ynyloxy-phenyl)-cyclohexyl]-2-phenyl-2-prop-2-ynyloxy-acetamide, 2-(4-chlorophenyl)-N-[trans-2-(3-methoxy-4-prop-2-ynyloxy-phenyl)-cyclohexyl]-2-prop-2-ynyloxy-acetamide, 2-(4-bromophenyl)-N-[trans-2-(3-methoxy-4-prop-2-ynyloxy-phenyl)-cyclohexyl]-2-prop-2-ynyloxy acetamide, and 2-(3,4-dichlorophenyl)-N-[trans-2-(3-methoxy-4-prop-2-ynyloxy-phenyl)-cyclohexyl]-2-prop-2ynyloxy-acetamide.

9. A process for the preparation of a compound of formula I according to claim 1, which comprises reacting an α-hydroxy- or α-alkoxy acid of formula II

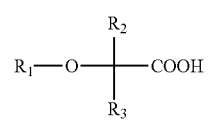

wherein R$_1$, R$_2$ and R$_3$ are as defined for formula I, or a carboxyl-activated derivative of the acid of formula II, is reacted with an amine of formula III wherein A, R$_4$, R$_5$ and R$_6$, are as defined for formula I, with an amine of formula III

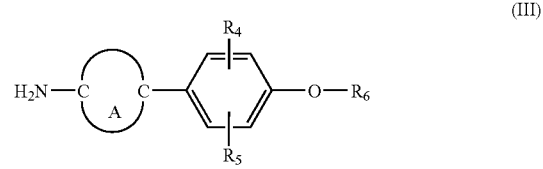

wherein A, R$_4$, R$_5$ and R$_6$, are as defined for formula I.

10. A process for the preparation of a compound of formula I wherein $R_1$ is as defined in claim 1 with the exception of hydrogen, which process comprises reacting an α-hydroxy acid derivative of formula Ia

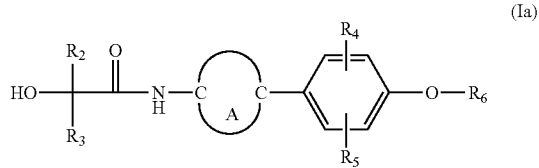
(Ia)

wherein A, $R_2$, $R_3$, $R_4$, $R_5$ and $R_6$ are as defined for formula I, with an alkyl-, alkenyl- or alkynylhalide of formula IV

(IV)

wherein $R_1$ is as defined for formula I, with the exception of hydrogen, and where X is a leaving group like a halide such as a chloride or bromide, or a sulfonic ester such as a tosylate, mesylate or triflate.

11. A process for the preparation of a compound of formula I wherein $R_6$ is as defined in claim 1 with the exception of hydrogen, which process comprises reacting a phenol of formula Ib

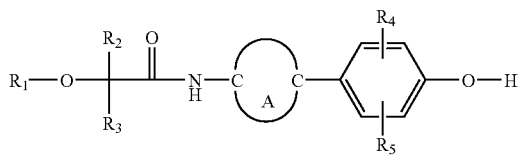
(Ib)

where A, $R_1$, $R_2$, $R_3$, $R_4$, and $R_5$ are as defined for formula I, with a compound of formula V

(V)

where $R_6$ is as defined for formula I but is not hydrogen and where Y is a leaving group like a halide such as a chloride or bromide or a sulfonic ester such as a tosylate, mesylate or triflate.

12. A composition for controlling and protecting against phytopathogenic microorganisms, comprising a compound of formula I according to claim 1 as active ingredient together with a suitable carrier.

13. A method of controlling and preventing an infestation of crop plants by phytopathogenic microorganisms, preferably fungal organisms, which comprises the application of a compound of formula I according to claim 1 as active ingredient to the plant, to parts of plants or to the locus thereof.

* * * * *